United States Patent
Wunderlich et al.

[11] Patent Number: 5,254,294
[45] Date of Patent: Oct. 19, 1993

[54] SOFT GELATIN CAPSULES

[75] Inventors: Jens-Christian Wunderlich, Heidelberg; Ursula Schick, Wiesloch; Jurgen Freidenreich, Schriesheim; Jurgen Werry, Ludwigshafen, all of Fed. Rep. of Germany

[73] Assignee: Alfatec Pharma GmbH, Heidelberg, Fed. Rep. of Germany

[21] Appl. No.: 876,863

[22] Filed: Apr. 30, 1992

[30] Foreign Application Priority Data

Jan. 17, 1992 [DE] Fed. Rep. of Germany ....... 4201178

[51] Int. Cl.⁵ .............................................. B29C 35/00
[52] U.S. Cl. ............................................. 264/4; 425/5
[58] Field of Search ..................... 264/4, 4.1, 4.3, 4.4; 425/5

[56] References Cited

U.S. PATENT DOCUMENTS

| | | | |
|---|---|---|---|
| 4,166,800 | 9/1979 | Fong | 264/4.4 |
| 4,426,337 | 1/1984 | Suzuki et al. | 264/4 |
| 4,981,625 | 1/1991 | Rhim et al. | 425/5 |

Primary Examiner—Jill L. Heitbrink
Attorney, Agent, or Firm—Omri M. Behr; Matthew J. McDonald

[57] ABSTRACT

In a dropping procedure for the formation of soft gelatin capsules in which, suitably, a pasty, fluid or sol/gel forming filling material is encapsulated with a soft gelatin mass, the solidification of the soft gelatin mass in a cooling bath of a chemically inert, exceedingly cold fluid which has no negative biological impact nor leaves harmful residue on the soft gelatin capsule. As cooling bath, there is most suitably utilized liquid nitrogen.

9 Claims, 1 Drawing Sheet

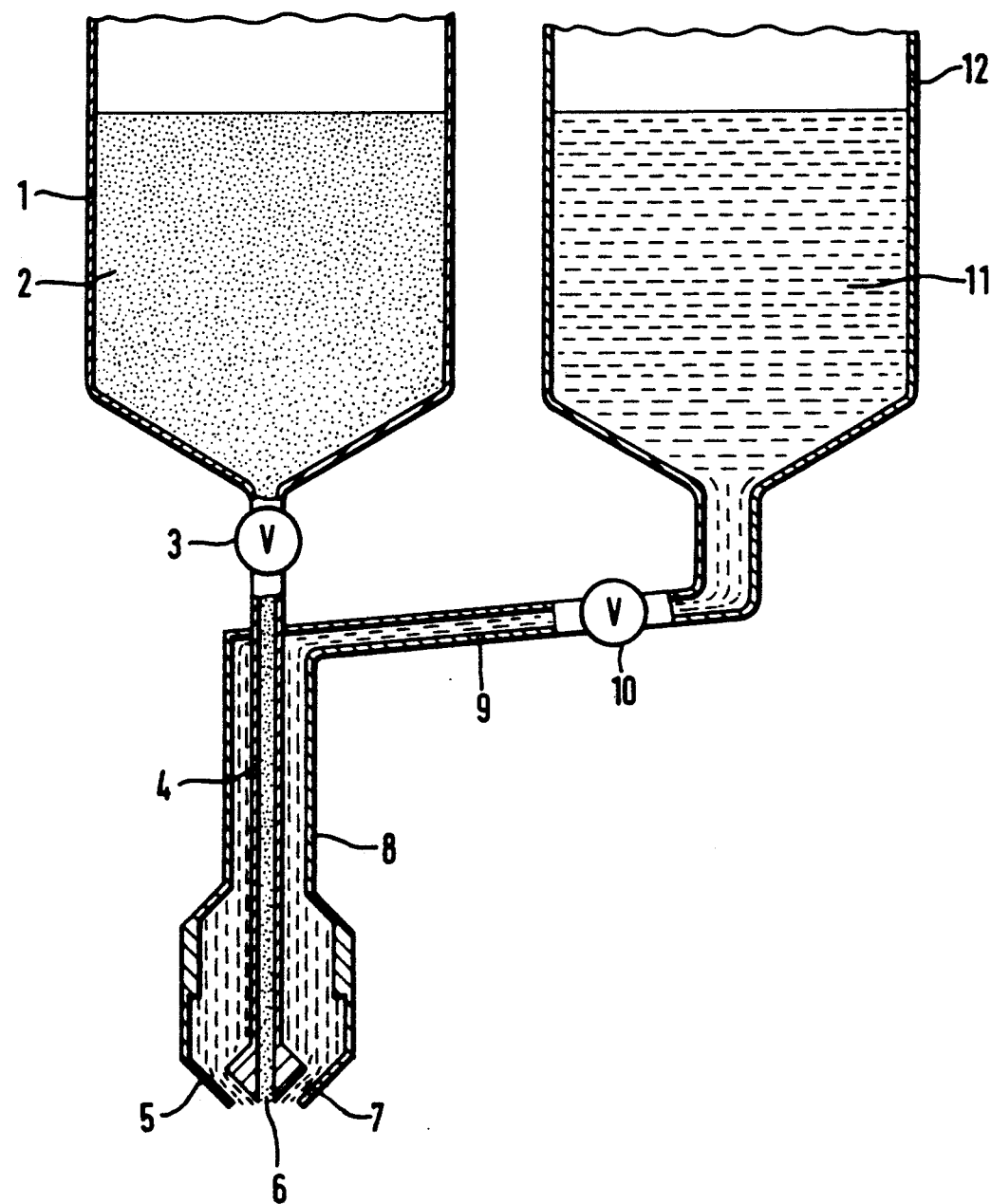

SOFT GELATIN CAPSULES

TECHNICAL FIELD OF THE INVENTION

The invention concerns a process for the preparation of soft gelatin capsules utilizing a drop process, whereby a paste-like or liquid filler is encapsulated with a soft gelatin mass, as well as the hardening of the gelatin mass in a cooling bath.

BACKGROUND OF THE INVENTION

The formation of soft gelatin capsules is today preferably carried out in a stamping process wherein the capsule wall is assembled from two gelatin halves which are stamped out of a gelatin band and then molded. Preferably, there is utilized the Scherer process operating under the rotary die method. Herein two endless gelatin bands run against two adjacent and mutually counter-rotating molding rollers. While the gelatin bands are being pressed into the molded and so create the capsule halves, the flowable filler is provided into the thus formed capsule through an exact dosing wedge. There follows the sealing together of the capsule halves, their stamping out, a wash procedure for the freeing of attached oil, a rotational dryer step as well as an adjacent shelf drying.

The rotary die method makes possible the formation and filling of capsules in a single work stream and provides a hourly yield of up to 100,000 pieces. A typical marker for the Scherer capsules is the essential weld seam in the longitudinal direction. The Scherer process has among others, the following disadvantages.

A) In order to produce soft gelatin capsules there can only be employed gelatins whose quality varies within rather narrow parameters. For example the following specifications must be met: The gelatin types must possess a gallert hardness of approximately 100 to 200 bloom as well as having viscosity values which remain thermostable over an extended time since when the gelatin bands are poured there must be provided an equal band thickness. Thus, the viscosities of the selected gelatin types cannot, over a time period of several days at 60°, drop by more than about 20 to 15%.

B) The molding rollers for the formation of the gelatin capsules from the two gelatin bands must be precisely made and operate very exacting. They are therefore expensive to make and sensitive to disturbance in operation.

C) In the process of preparation of soft gelatin capsules, it is necessary to provide a climatic environment of from 20 to 30% relative humidity at 22° as may be deduced from the absorption isotherm of water to the gelatin capsule material. Hence, the production and packing rooms must be totally air conditioned.

D) The technique of soft gelatin capsule production, in addition to the aforementioned substantial requirements of material and air conditioning, so much know-how that only those producers specializing therein can cope with it.

E) A further disadvantage lies therein that during the stamping step, the remaining portions of the gelatin bands, the so-called net wastes, can only be reutilized to a minimal extent (about 5%) and thus up to 60% of the originally charged gelatin mass must be disposed of. These net residues are, because of the requirements of the process, contaminated with separating oils and where highly active substances are utilized as the filler material, a contamination of the stamped-out net cannot be avoided. Thus, such net residues must be treated as special waste. Furthermore, these waste materials contain substantial amount of colored pigments which make the recovery of the starting material impossible.

F) Because of production process requirements, the finished capsule is coated with a contaminating separation oil which must be removed by means of a lipoid solvent material such as cheerio, methylene chloride and the like. This process step requires technical and capital intensive expenditures in order to avoid any contamination of the soft gelatin capsules and the surrounding atmosphere by the physiologically harmful solvents. Furthermore, the treatment of soft gelatin capsules containing pharmaceutically active materials with such harmful solvents, can also cause problems since the user of the soft gelatin capsules before ingesting the thus handled soft gelatin capsules could shy away from them.

A further process for the formation of soft gelatin capsules which is well known in the art is the drop and blow process, which has been called the Globex process after its developers. Herein, a lipophilic filler material is dropped out of a jet while at the same time, warm gelatin solution flows out of a tube surrounding said jet. When dropped into a cooling fluid of predetermined density (for example paraffin oil) surface tension causes these capsules to take up a spherical shape and to solidify. Oily carrier materials are suitable as the filler substance. This process delivers seamless round capsules at a hourly production rate of up to 70,000 pieces. This drop or blow process has certain disadvantages of which the following are the most important:

a) Only oily substances can be used as the filling material.

b) The different components required by the process technology such as the oily filling material, the gelatin mass, and the cooled quenching bath (paraffin oil) can be harmonized with each other, only with considerable difficulty, since one is here concerned with a 3-phase system.

c) The residual quenching bath material (paraffin oil) must be removed with a solvent. This gives rise to the same problems as occur under Section (F) of the stamping process.

It is thus clear that the procedures known to the art for the production of soft gelatin capsules are subject to technological and economic problems. The complex requirements of the process technology create considerable difficulties for the pharmaceutical manufacturing companies who wish to install and run a production system for soft gelatin capsules. Additional problems can arise due to the lack of knowledge of the properties of gelatin. Furthermore, problems arise in the cleaning of the residual separation oil or cooling oil from the capsules, to which is added, in the Scherer process, the substantial additional burden of disposal of the net wastes.

The purpose of the present invention is to avoid the problems which arise in the production of soft gelatin capsules under the state of the art, in particular the provision of a technologically and economically relatively simple process, which a pharmaceutical production company can utilize without a great expenditure on equipping and running a production facility for soft gelatin capsules.

This task is solved thereby that in a process of the prior art, there is utilized a cooling bath of exceedingly cold fluid, for example liquid nitrogen.

In particular, the present invention provides a process for the preparation of soft gelatin capsules in a dropping process wherein the filler material is surrounded with a soft gelatin mass and inserted into a cooling bath, characterized thereby that there is utilized the cooling bath for the molding of the capsules comprises an exceedingly cold fluid which has neither any biologically hazardous or harmful residued. For the practice of the present process, twin material jets, for example concentric double capillaries, such as are used in the Globex process or are known from the "Sepharex" capsule machine of the Freund Company, may be utilized. The warmed coating material (soft gelatin mass) thus flows in the outer and the filling material in the inner capillary. The separation of the capsules can, where necessary, be timed pulse-wise or intermittently controlled.

BRIEF DESCRIPTION OF THE DRAWINGS

There is illustrated:

FIG. 1—A cross-sectional view of a dosage arrangement utilized for the process of the present invention.

In FIG. 1, there is provided a schematic representation of a dosage arrangement with twin material jets.

In the heatable gelatin container 12, there is provided the capsule wall material 11. The second container 1 comprises the filling material 2. The amount of material supplied can be regulated by the controllable dosage arrangement 3 and 10. The coating and filling materials flow over the provision tubes 9 and 10 into the jet 7, wherein the gelatin solution is so led via tubular shell 8 that it covers the filling material coming out of the inner jet head 6 via the adjustable jet surround 5. An intermittent or pulsed timed flow arrangement causes the formation of the capsules.

Thereafter, the capsules are fed to an insulated drop freezer containing an exceedingly cold fluid in the region of $-70°$ C. to $-220°$ C. and having a boiling point of between $-70°$ C. and $-220°$ C., such as, for example, liquid nitrogen. In this location the actual molding process occurs. Because of the extreme temperature difference between the warmed gelatin/coating material and the fluid, gas immediately evaporates and surrounds the capsule with a gas buffer which exercises an even pressure upon the capsule. The capsule thus assumes a spherical format and freezes.

The thus formed seamless capsules are transported out of the dip bath by means of a transport band and after melting in a conventional manner, are dried directly, that is to say, without the cleaning steps required with organic solvents in the usual process.

In accordance with a particular embodiment, the gelatin coating can contain a pharmaceutically active substance, suitably the gelatin capsule contains a pharmaceutically active substance which is different from the filling material, which is advantageous, for example, for the avoidance of incompatibilities between pharmaceutically active materials.

In such a manner by provision of a pharmaceutically active material in the coating itself, one can develop a delayed action formulation with the initial dose, whereby the initial dose is located in the coating and the filling material contains the active substance in a delayed release form. Further preferred embodiments of the process of the present invention are set forth in the sub subclaims and claimed therein.

A further advantage of the claimed process with respect to the rotary die dye, as well as the stamping process, resides therein the gelatin with bloom figures of between 80 and 300 may be utilized.

There may be used gelatins, fractionated gelatins, or collagen.

For the formation of the soft gelatin mass there may be utilized all known softening agents, for example glycerine, sorbitol, etc., in the amount of between 0.1 to 50% (relative to the prescription mass). There may also be used all conventional additives for capsule coatings (colorants, opacifiers, pigments, odorants and sweetening materials, preservatives, and so on), in an amount of from 0.1 to 30% (with respect to the prescription mass).

The soft gelatin masses can be coated in a conventional manner with gastric juice resistant materials in an subsequent coating procedure, in order to make them stomach-acid resistant.

In accordance with the process of the present invention, materials selected from the group consisting of polyacrylic acids and their mixed polymers, methacrylic acids and their mixed polymers, cellulose acetophthalate in the range of 1 to 20%, relative to the prescription mass, can be directly incorporated into the soft gelatin mass in the form of a water soluble salt. Such a mode of proceeding yields a product which complies with the appropriate requirements of the Pharmacopeas (DAB, USP).

A controlled release can advantageously be obtained in the following manner. The filling material, for example a collagen hydrolysate or gelatins is treated with a pharmaceutically acceptable cross-linking agent, for example aldoses or citrale.

As filling material, there may be used all pharmaceutical materials or filing prescriptions which have heretofore been usable in classically produced soft gelatin capsules. These are principally fluid filler materials, for example, etheric oils (pinene, meytol, peppermint oil, etc), oily substances such as Vitamin E, or cod liver oil, garlic oils, omega-3 fatty acids), primrose candle oil made of oenothera bienis, Juniper oil, St. John's wart oil, wheat germ oil, lecithin, etc). These lipophilic materials can be provided in the form of microemulsions in the appropriate prescription mass.

Aqueous pharmaceutically active materials may be utilized in the invention by means of a filling material of collagen hydrolysate or gelatins which contain a softening additive in the same concentration as the capsule wall. In this way, one can avoid diffusion of the softening agent in the cell wall into the filling material.

As softening agents, there may be used any member selected from the group consisting of glycerol, polypropylene glycol, polyethylene glycol, triacetin, sorbitol, sorbitan mixtures as well as mixtures thereof.

Substantially water insoluble pharmaceutical materials can be brought into the filling material, in the manner known to the art, i.e., utilizing solvating agents.

The advantage with respect to the dropping or blowing processes rests in the fact that not only oily but also pasty and readily flowable materials can be utilized as the filling material (oily suspensions, plant extracts, rutin, beta carotene, mineral materials, vitamin A/C/E combinations and so on), or fillers which solidify at room temperature (suitably soft gelatin masses), that is to say, those that are semi-solid, may be utilized.

Because of the shock production nature of the dip freezing, the combination of the filling material and the encapsulating gelatin solution do not require special attention to be paid to their mutual rheological properties as is necessary with the different densities of the three-phase fill material-gelatin material-drop bath of the prior art.

Further embodiments of the present invention are set forth in the United States application for Letters Patent as set forth herein, whose disclosure is incorporated application for Letters Patent as set forth herein, whose disclosure is incorporated herein by reference. These parallel U.S. applications have been filed in the United States Patent and Trademark Office by the same inventors on the same day and are as follows:

Title: "Aloe Vera Juice Containing Pellets for Production Thereof and the Use Thereof as Pharmaceutical Cosmetic and Peroral Agents", U.S. Ser. No. 07/876,876.

Title: "Pellets Containing Peptides, Method of Making Same and Use Thereof", U.S. Ser. No. 07/876,865.

Title: "Means for Containing Active Substances Having a Shell of Hydrophilic Macromolecules, Active Substances and Process for Preparation Thereof", U.S. Ser. No. 07/876,864.

Title: "Pellets Containing Plant Extracts, Process of Making Same and Their Pharmaceutical Peroral or Cosmetic Use", U.S. Ser. No. 07/876,866.

Title: "Peroral Dosage Form for Peptide Containing Medicaments, in Particular Insulin", U.S. Ser. No. 07/876,867.

Title: "Pellets Containing Dihydropyridine Derivatives Process for Production Thereof and Use as Rapid Action Dosage in Heart and Circulatory Diseases", U.S. Ser. No. 07/876,877.

Thus in contrast the Globex procedure, it is possible, by means of the present invention, to encapsulate prescriptions as the filling material on the basis of cold water soluble gelatins or gelatin itself. The spherical state of the capsules is formed by the systems. When for example, the same amounts of softeners are utilized in the coating as in the gelatin containing filling material, a similar residual moisture content is present in the entire capsule after drying.

The above-identified "solid" fillers in conjunction with hydrophilic carrier materials in the capsules, provide the possibility for delayed release of pharmaceutically active materials. Thus for example, by utilizing particular types of gelatin for the filling prescription, which have a softening point above 37°, it is possible to formulate a matrix for the pharmaceutically active material whose degradation is time controlled. The aforementioned "solid" fillers are furthermore suitable to contain stable emulsions, pharmaceuticals dissolved in water and microcapsules.

Furthermore, in addition to the usual soft gelatin mass, additional materials in particular polymeric macromolecules, suitable for the controlled release of the filling material may be added; for example there may be utilized alginates, pectins, thermoreversable alginate gels, agar, albumins, casein, plant proteins, gum arabic, xanthane, tragacanth, chitosan, polyethylene glycol, natural and modified starches, maltodextrin, methylcellulose, cellulose ether polysaccharides, carboxymethyl celluloses, etherized carboxymethylcelluloses, hydroxy propylcellulose, hydroxy propylmethylcellulose phthalate, cellulose acetophthalate, polyvinyl alcohol, polyvinylpyrrolidone, polyacrylic acid, mixed polymers of methacrylic acid and methacrylic acid esters, aldoses, citral, in different proportions and mutual mixtures.

As the exceedingly cold fluid, there may be utilized any fluid in which the gelatin mass solidifies immediately and which leaves no harmful residue on or in the soft gelatine capsule. Particularly desirable in this respect is liquid nitrogen.

Further exceedingly cold fluids which may be utilized in the process of the present invention are, for example, liquid gases such as argon or liquid air or the like.

Thus, by means of the process of the present invention, there may be produced the soft gelatin capsules which, in addition to pharmaceutically active materials, may be utilized for dietetic foods or for cosmetics, for example bath oil containing capsules or concentrates containing encapsulated active materials.

Furthermore, the mode of production in accordance with the present invention, avoids the need for expensive, disturbence sensitive precision rollers. The technology is so simple that only a very small expenditure is required for the apparatus and for carrying out the process and the required no-how is substantially easier to acquire. There is no large production of waste gelatin. The expensive air conditioning of the production rooms can be ignored. The thus produced gelatin capsules are seamless. By the provision of a plurality of adjacent production apparatuses, it is possible to raise the hourly production to virtually any desired level.

As a substantial advantage of the present process, one need no longer be concernedwith the cleaning of the completed soft gelatin capsules to remove adhering oils (separation oil between the rollers and the gelatin bands or paraffin oil from the quenching bath), which are necessary in all of the procedures presently known to the art). Thus, it is no longer necessary to enter into the substantial equipment expenditure required by the present state of the art. The problems which are raised during the handling of pharmaceutically active soft gelatin capsules by harmful and ecologically destructive solvents and the removal of said solvents from the discharged air, are entirely absent in the suggested process. Furthermore, the exceedingly cold fluids which are utilized and which are suitable for the process such as, for example, liquid nitrogen, are totally chemically inert.

EXAMPLE 1

Prescription for the Coating

Gelatin 250 bloom, 2.5 parts
Glycerol (85%), 1 part
Water, 6.5 parts.

Prescription for the Filling

D, L-alpha-tocopheryl acetate—1 part
Soya bean oil—1 part.

The gelatin granulate is preswollen for 30 minutes and then dissolved at 60° C. Glycerol is then added under stirring. After degassing in a vacuum, the thus produced mass is in the storage container 11, which is heated to 60° C., is lead to the previously described twin jet arrangement of FIG. 1. To a storage container 2, which is similarly heated to 60° C. is charged a solution, at a similar temperature, of the tocopheryl acetate in soya bean oil is charged. Via the jacket pipe 8, the gelatin solution is so provided that, via the jacket jet 5, it coats the filling material flowing out of the inner jet head 6. The filling material is provided via the feed pipe 4. The capsules are timed with a dose of 150 mg of tocopheryl acetate per capsule, which are cut off and dropped into the dropping bath filled with liquid nitrogen. These solidify immediately in a hard spherical shape and are transported via a transport band into a storage container. After thawing, they are dried down to a residual moisture content of between 7 and 8% in the conventional manner (1 to 2 hours drying tumbler drying and then in an air recirculation dryer down to the 7 to 8% residual water content).

EXAMPLE 2

Content of the Capsule Shell

Gelatin 160, bloom—13 parts
Glycerol—15 parts
Iron oxide—0.1 part
Water—54.9 parts.

The capsule shell material is produced in accordance with Example 1 in which the iron oxide suspended in the solution. As filling material, polyethylene glycol 4000 is mixed with polyethylene glycol 400 and warmed to 60°. Aerosil and the active material are suspended therein, both mixtures are filled into the appropriate storage containers which have been heated to 60° C.

Components of the Filler

Polyethylene glycol 400—90 parts
Polyethylene glycol 4000—2 parts
Aerosil—8 parts
Indomethacin—25 mg. (This is an error here).

The pharmaceutically active material is homogeneously mixed with the carrier mass and in analogy to Example 1, is dropped into liquid nitrogen bath to form capsules containing 25 mg. of Indomethacin.

We claim:

1. A process for the preparation of soft shaped gelatin capsules containing a filling material by a dropping procedure comprising the steps of coating said filling material with a soft gelatin mass to form a coated material, forming droplets of said coated material and causing said droplets to fall into a cooling bath which contains an exceedingly cold liquid having a boiling point of between −70° C. and −220° C. which has no negative biological influence or leaves no harmful residue upon the soft gelatin capsules, wherein said droplets are shaped and solidified into capsules.

2. The process in accordance with claim 1 wherein the cooling bath comprises a mixture of methanol and dry ice.

3. The process according to claim 1 wherein the cooling bath comprises liquid nitrogen.

4. The process according to claim 1 wherein the filling material is a member selected from the group consisting of pharmaceutically active materials, active substances, dietetic foods, cosmetics, liquid materials, pasty materials, materials with suspended components, emulsions, micro-encapsulated materials, as well as mixtures thereof.

5. The process according to claim 1 comprising the additional step of adding a softening agent to the filler, said agent being selected from the group consisting of glyceryl, propylene glycol, polyethylene glycol, triacetin, sorbitol, sorbitan mixtures, as well as mixtures thereof.

6. The process according to claim 4 wherein the filling material and the gelatin shell comprise softeners in substantially the same concentration.

7. The process according to claim 1 wherein as a gelatin, there is used a gelatin having a bloom value of from about 50 to 300 bloom.

8. The process according to claim 6 wherein the gelatins are utilized which are selected from the group consisting of fractionated gelatins, gelatin derivatives, collagen hydrolysate, as well as mixture thereof.

9. The process according to claim 1 wherein materials are added to the filling material in which enable controlled release of that filling material, said materials being selected from the group consisting of poly- and methyl-acrylic acid derivatives, alginates, aldoses, citral, cellulose derivatives, polyethylene glycol, polyvinyl alcohol, polyvinyl pyrrolidone, agar agar, pectins and the mixtures thereof.

* * * * *